(12) United States Patent
Kim

(10) Patent No.: US 7,713,549 B2
(45) Date of Patent: May 11, 2010

(54) EXTENDED RELEASE PERFORATED TABLET

(75) Inventor: Cherng-ju Kim, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 985 days.

(21) Appl. No.: 11/479,844

(22) Filed: Jun. 30, 2006

(65) Prior Publication Data

US 2008/0003287 A1    Jan. 3, 2008

(51) Int. Cl.
*A61K 9/20* (2006.01)
*A61K 9/24* (2006.01)
*A61K 9/28* (2006.01)

(52) U.S. Cl. ............... 424/472; 424/464; 424/465; 424/471; 424/474

(58) Field of Classification Search .................. None
See application file for complete search history.

(56) References Cited

U.S. PATENT DOCUMENTS

| | | | |
|---|---|---|---|
| 4,361,545 A | 11/1982 | Powell et al. | |
| 4,606,909 A | 8/1986 | Bechgaard et al. | |
| 4,775,536 A | 10/1988 | Patell | |
| 5,162,117 A | 11/1992 | Stupak et al. | |
| 5,431,920 A | 7/1995 | Bechard | |
| 5,783,212 A | 7/1998 | Fassihi et al. | |
| 5,817,338 A | 10/1998 | Bergstrand et al. | |
| 5,945,125 A | 8/1999 | Kim | |
| 5,962,024 A | 10/1999 | Marvola et al. | |
| 6,068,859 A | 5/2000 | Curatolo et al. | |
| 6,110,500 A * | 8/2000 | Kim | 424/475 |
| 2005/0025829 A1 * | 2/2005 | Kim | 424/471 |

OTHER PUBLICATIONS

Kim, Cherng-Ju, Compressed Donut-Shaped Tablets with Zero-Order Kinetics, Pharmaceutical Research, vol. 12, No. 7, 1995, pp. 1045-1048.
Kim, Cherng-Ju, Release kinetics of coated, donut-shaped tablets for water soluble drugs, European Journal of Pharmaceutical Sciences, 7, 1999, pp. 237-242.
International Search Report and Written Opinion, International Patent Application No. PCT/US06/20976, Mailing Date Oct. 5, 2006.
U.S. Appl. No. 11/443,666, Kim, C.

* cited by examiner

*Primary Examiner*—S. Tran
(74) *Attorney, Agent, or Firm*—Ray F. Cox, Jr.

(57) ABSTRACT

A tablet for the controlled release of a pharmaceutically active ingredient. The tablet is in the form of coated DST's and MLDST's so that immediate release or time-delayed release can be achieved. Further, such extended release DST's and MLDST's may provide zero order or first order extended release kinetics depending on the excipients and types of pharmaceutically active ingredients in the tablet formulation. The time delay coating is made of high molecular weight water soluble polymers so that dose dumping can be minimized even when the hydrated surface of the DST and MLDST peels off. A second coating of low molecular weight water soluble polymer with a pharmaceutically active ingredient dispersed therein provides for pulsatile release.

2 Claims, 8 Drawing Sheets

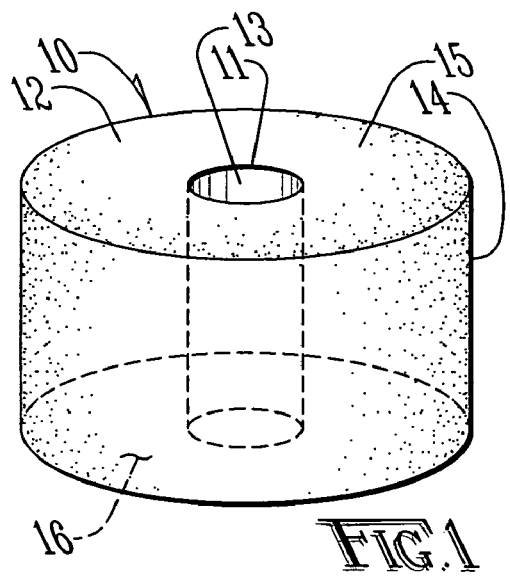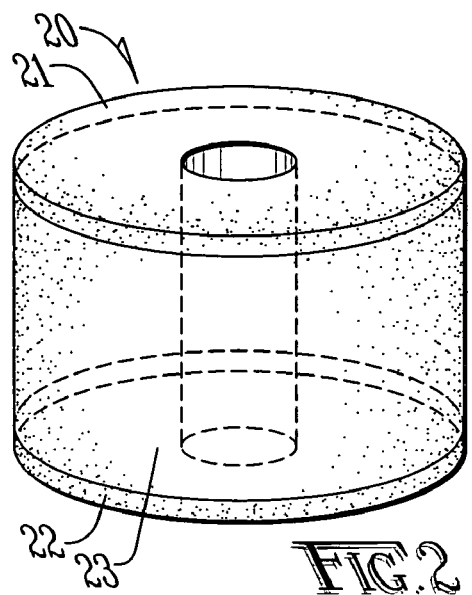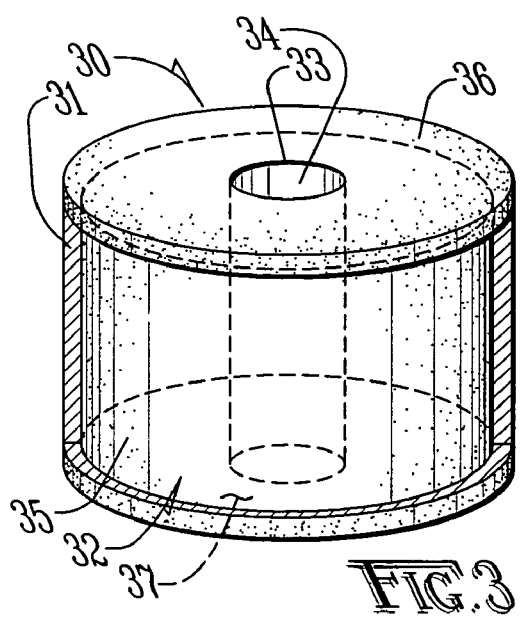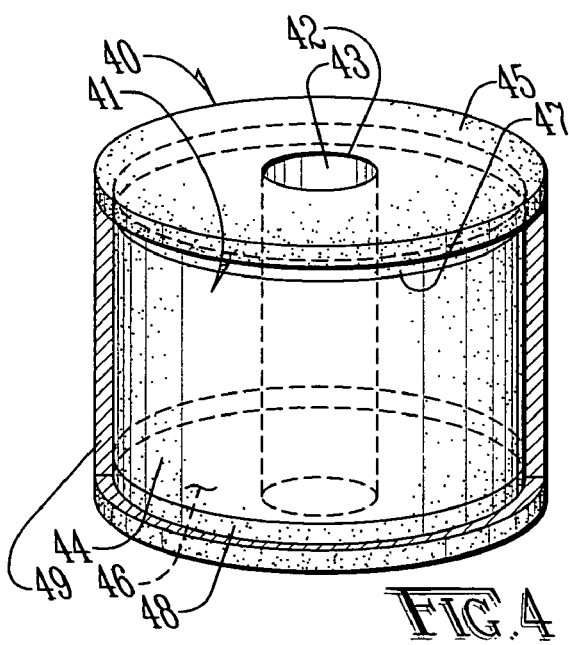

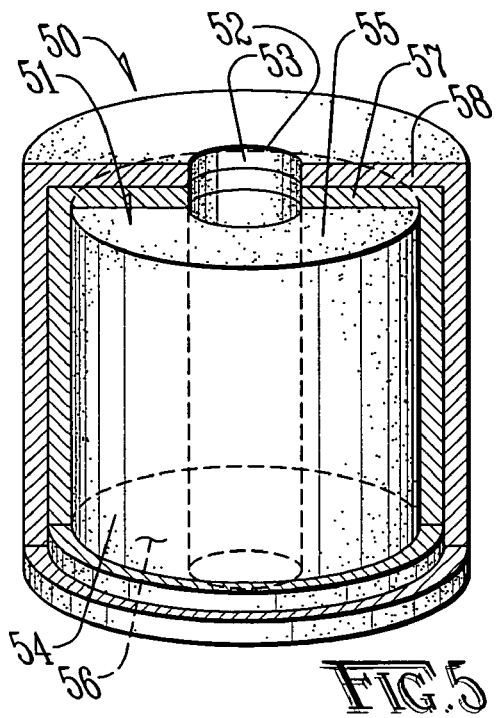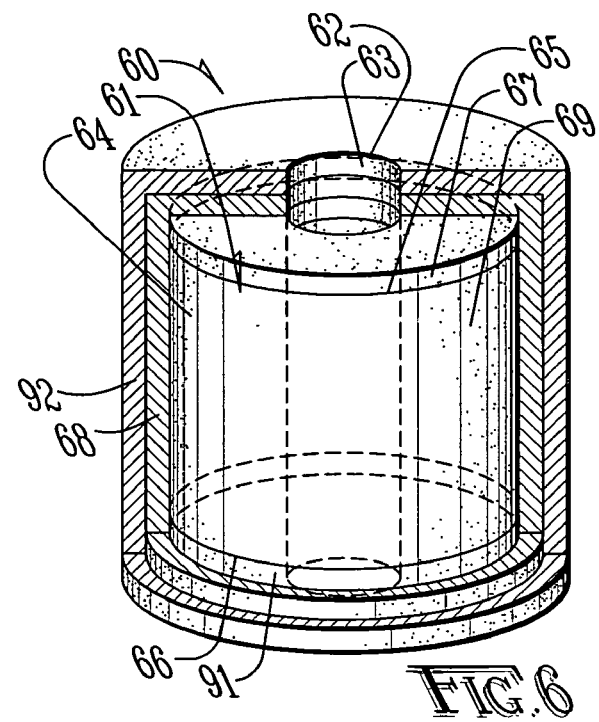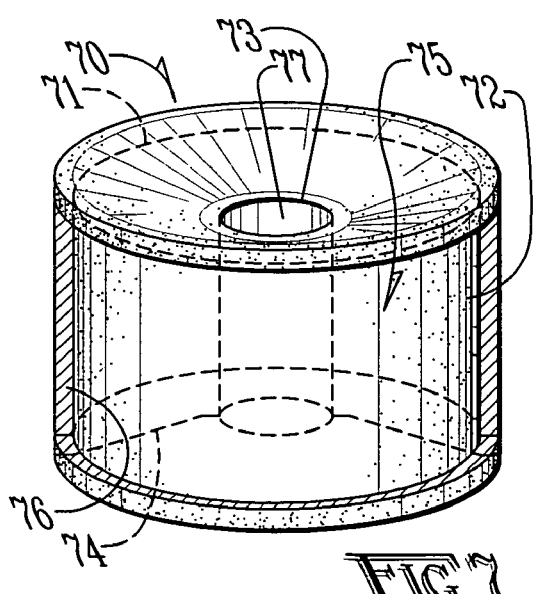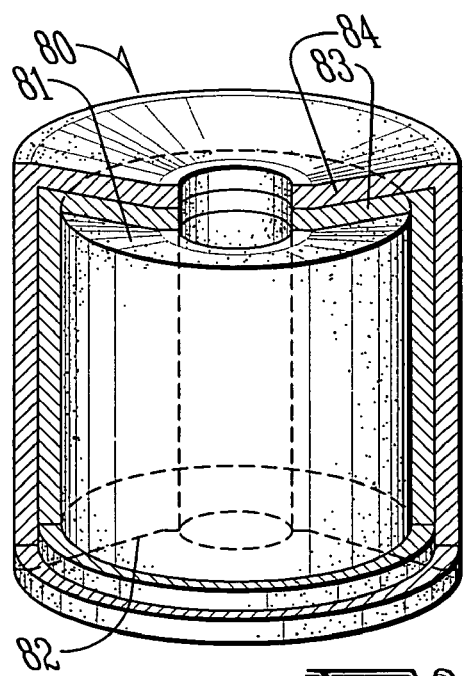

EXTENDED RELEASE PERFORATED TABLET

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention relates to pharmaceutical dosage forms and in, particular, to a coated perforated or donut-shaped tablet for extended release of a pharmaceutically active ingredient.

2. Brief Description of the Related Art

There have been various attempts made to create extended release dosage forms for orally administering pharmaceutically active ingredients. The terms "drug" and "pharmaceutically active ingredient" are used interchangeably herein. Some dosage forms tend to release a drug at rates that do not correlate well with the needs of the patient. For example, a particular dosage form may release a large amount of a drug rapidly upon ingestion where a more constant rate of release is desirable. In other situations, varying release rates may be desirable. Additional background information on the art of controlling release rates of drugs in orally administered dosage forms is found in U.S. Pat. Nos. 5,945,125 and 6,110,500 and U.S. Published Patent Application No. US2005/0025829, the disclosures of which are incorporated herein by reference. Dosage forms typically comprise the drug; that is, the pharmaceutically active ingredient, dispersed in various excipients including polymers whose rates of dissolution are known. As the tablet is dissolved, the drug is released at a predicted rate. Coating excipients having various rates of dissolution have also been used for time delayed release of drugs.

Common oral extended release or pulsatile release dosage forms include tablets, caplets, and capsules containing small spherical pellets. Such dosage forms typically have the combined geometry of slabs and cylinders, which tend to produce varying release rates. Due to the shape, a cylindrical tablet does not follow zero order release kinetics. As the tablet is dissolved, the amount of surface area exposed to the dissolution medium changes, thereby changing the rate at which the dissolution occurs and thus the drug release rate decreases with drug release time.

When a central perforation or hole is made in an extended release tablet (donut-shaped tablet (DST)), the DST exhibits a constant drug release rate over time because a constant surface area can be radially maintained. A multi-layer DST (MLDST) can also be made as described in U.S. Published Patent Application No. US2005/0025829.

While constant drug release rates are desirable in certain circumstances, it is more generally desirable to be able to customize the kinetics of drug release. For example, a rapid initial release (a burst) may desirably be followed by a period of constant release. In other examples, it might be desirable to delay the release of the drug for a period of time or to release a pulse of the drug after a period of time delay or a period of constant release.

Hydrophilic polymers are commonly employed in extended release tablets. A problem associated with hydrophilic polymer based pharmaceutical compositions in a DST or MLDST is that these tablets can dose dump, that is, when not fully hydrated the hydrophilic polymers become very viscous and adhere to solids and biological surfaces. The surface of the tablet then peels off and the drug dosage is dumped into the patient.

BRIEF SUMMARY OF THE INVENTION

The present invention uses coated DST's and MLDST's so that immediate release or time-delayed release can be achieved. Further, such extended release DST's and MLDST's may provide zero order or first order extended release kinetics depending on the excipients and types of drugs in the tablet formulation. The coating layer for time delay is made of high molecular weight water soluble polymers so that the dose dumping can be minimized even when the hydrated surface of the DST and MLDST peels off. Low molecular weight water soluble polymer coatings having a drug dispersed therein may be employed to provide a pulsatile release of a drug.

These and other features and advantages of the present invention will become better understood from the following description, appended claims and accompanying drawings.

BRIEF DESCRIPTION OF THE DRAWINGS

FIG. 1 is top side perspective view of a donut-shaped tablet having a central perforation or hole as known in the prior art (DST).

FIG. 2 is a top side perspective view of a layered perforated tablet as known in the prior art (MLDST).

FIG. 3 is a top side perspective view of a coated perforated tablet according to one embodiment of the present invention, where the coating is a high molecular weight polymer without a drug dispersed in the coating. The coating is shown in partial cross section.

FIG. 4 is a top side perspective view of a coated layered perforated tablet accordingly to another embodiment of the present invention, where the coating is a high molecular weight water soluble polymer without a drug dispersed in the coating. The coating is shown in partial cross section.

FIG. 5 is a top side perspective view of a coated perforated tablet according to another embodiment of the present invention, where an inner coating comprises a high molecular weight water soluble polymer without a drug dispersed therein and an outer coating comprises a low molecular weight water soluble polymer with a drug dispersed therein. The coatings are shown in partial cross section.

FIG. 6 is a top side perspective view of a coated layered perforated tablet according to another embodiment of the present invention, where an inner coating comprises a high molecular weight water soluble polymer without a drug dispersed therein and an outer coating comprises a low molecular weight water soluble polymer with a drug dispersed therein. The coatings are shown in partial cross section.

FIG. 7 is a top side perspective view of a coated perforated tablet with sloped upper and lower surfaces according to another embodiment of the present invention, where the coating comprises a high molecular weight polymer without a drug dispersed therein. The coating is shown in partial cross section.

FIG. 8 is a top side perspective view of a coated perforated tablet with sloped upper and lower surfaces according to another embodiment of the present invention, where an inner coating comprises a high molecular weight water soluble polymer without a drug dispersed therein and an outer coating comprises a low molecular weight water soluble polymer with a drug dispersed therein. The coatings are shown in partial cross section.

DETAILED DESCRIPTION OF THE INVENTION

Figure 9:
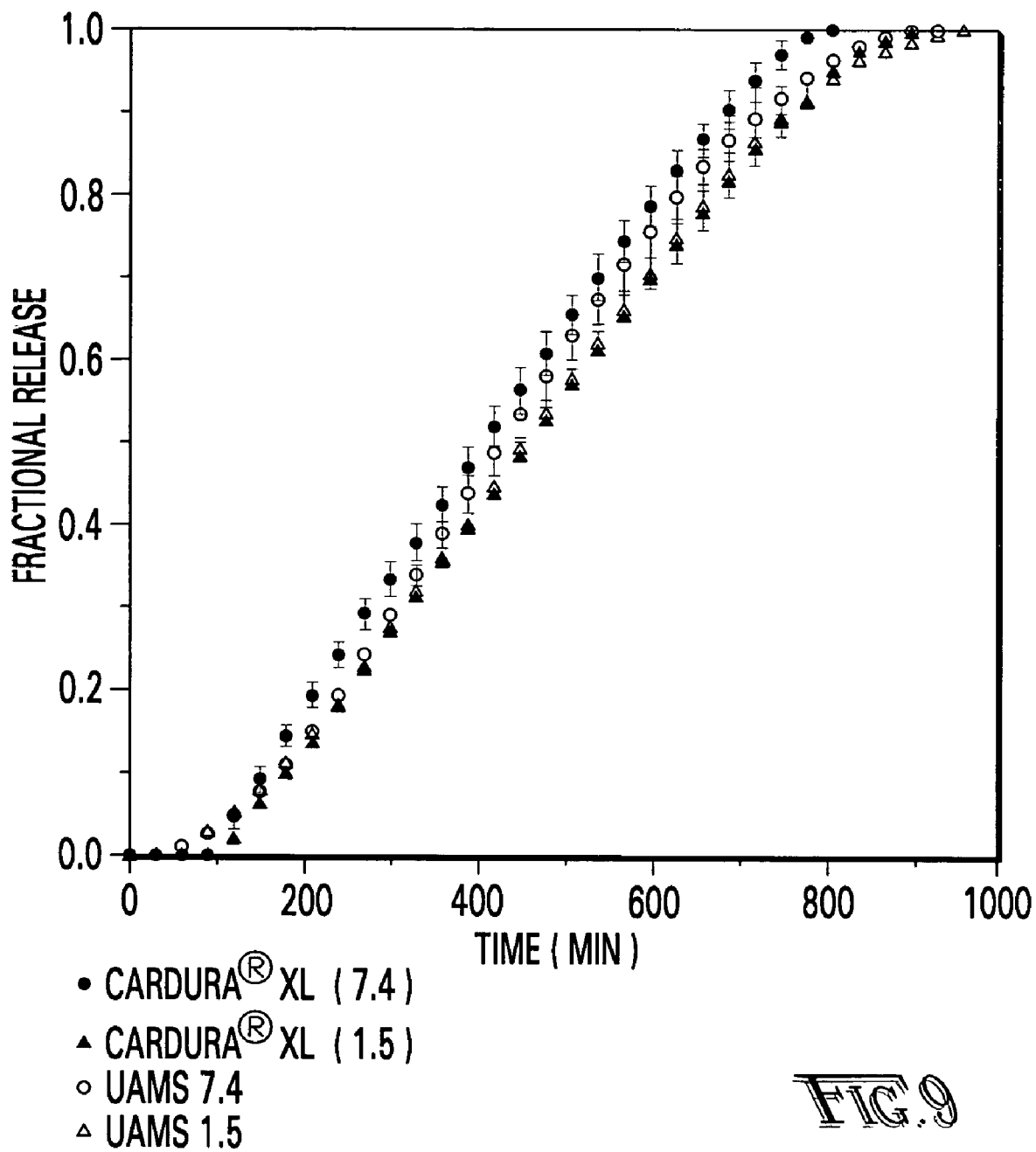
FIG. 9 is a graph of the release rate of doxazosin mesylate from the embodiment of the tablet of FIG. 3 superimposed on a graph of the release rate of a commercially-available brand of doxazosin mesylate, Cardura® XL (Pfizer Inc., New York, N.Y. USA).

The preferred embodiments of the invention are described herein with reference to FIGS. 1-14.

FIG. 1 is top side perspective view of a perforated or donut-shaped tablet 10 having a central perforation or hole 11 as known in the prior art (DST). The perforated tablet 10 comprises a core 12 through which the hole 11 penetrates. The core 12 is defined by a surface comprising an inner radial surface 13 surrounding the hole 11, an outer radial surface 14, an upper lateral surface 15 extending between an upper margin of the inner radial surface and an upper margin of the outer radial surface 14 and a lower lateral surface 16 extending between a lower margin of the inner radial surface 13 and a lower margin of the outer radial surface 14. The core 12 comprises at least one pharmaceutically active ingredient dispersed in at least one excipient. The selection of excipients allows some control in the release kinetics for the pharmaceutically active ingredient. Furthermore, it is known that perforated tablets of the type described have substantially zero order release kinetics.

FIG. 2 is a top side perspective view of a layered perforated tablet 20 as known in the prior art (MLDST). The layered perforated tablet 20 may comprise a plurality of layers. The character and composition of the layers may be selected for various release kinetics. For example, as described in U.S. Published Patent Application No. 2005/0025829 and shown in FIG. 2, an upper layer 21 and a lower layer 22 may comprise either water soluble or water insoluble polymers and an inner layer 23 may comprise a drug dispersed in an enteric polymer. Layering gives time for the tablet to hydrate to avoid dose dumping.

FIG. 3 is a top side perspective view of a coated perforated tablet 30 according to one embodiment of the present invention having a coating 31 of a high molecular weight polymer. The coated perforated tablet 30 has core 32 with a hole 33 extending through the core 32 as described above with reference to FIG. 1. The core 32 has a surface defined by an inner radial surface 34 surrounding the hole 33, an outer radial surface 35, an upper lateral surface 36 extending between an upper margin of the outer radial surface 35 and an upper margin of the inner radial surface 34, and a lower lateral surface 37 extending between a lower margin of the outer radial surface 35 and a lower margin of the inner radial surface 34. The core 32 comprises at least one pharmaceutically active ingredient dispersed in at least one excipient. The coating 31 is high molecular weight water soluble polymer substantially covering the outer radial surface 35, the upper lateral surface 36 and the lower lateral surface 37. The inner radial surface 34 is not covered. The coating 31 does not contain a pharmaceutically active ingredient. The high molecular weight polymer preferably has a number-average molecular weight of at least 10,000. Although the inner radial surface 34 is exposed to the dissolution medium shortly following ingestion, the coating 31 provides a time delay before the outer radial surface 35, the upper lateral surface 36 and the lower lateral surface 37 are exposed to the dissolution medium. The amount of the time delay may be adjusted by the appropriate selection of the specific polymer, the specific number-average molecular weight and the thickness of the coating 31. The time delay allows the tablet time to hydrate to prevent dose dumping. Furthermore, since the coating 31 does not contain a pharmaceutically active ingredient, even if the coating 31 peels off from the tablet, there will be no dose dumping.

Figure 10:
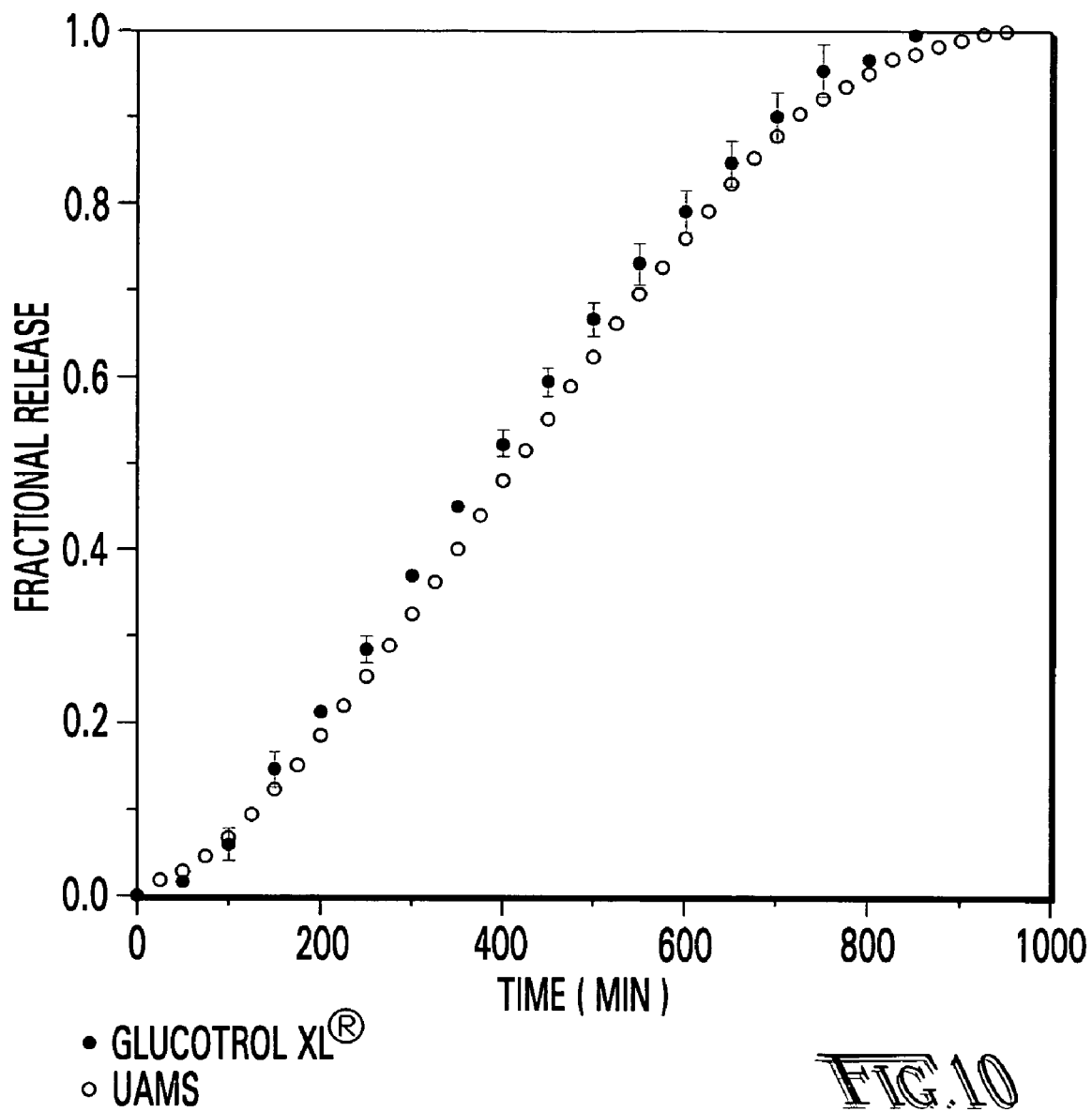
FIG. 10 is a graph of the release rate of glipizide from the embodiment of the tablet of FIG. 3 superimposed on a graph of the release rate of a commercially-available brand of glipizide, Glucotrol XL® (Pfizer Inc., New York, N.Y. USA).

FIG. 9 is a graph of the release rate of doxazosin mesylate from the embodiment of the tablet of FIG. 3 superimposed on a graph of the release rate of a commercially-available brand of doxazosin mesylate, Cardura® XL (Pfizer Inc., New York, N.Y. USA). FIG. 10 is a graph of the release rate of glipizide from the embodiment of the tablet of FIG. 3 superimposed on a graph of the release rate of a commercially-available brand of glipizide, Glucotrol XL® (Pfizer Inc., New York, N.Y. USA).

FIG. 4 is a top side perspective view of a coated layered perforated tablet 40 accordingly to another embodiment of the present invention, where the coating 49 is a high molecular weight water soluble polymer. The embodiment of FIG. 4 is similar to the embodiment of FIG. 3 described above. The coated layered perforated tablet 40 of FIG. 4 has core 41 with a hole 42 extending through the core 41. The core 41 has a surface defined by an inner radial surface 43 surrounding the hole 42, an outer radial surface 44, an upper lateral surface 45 extending between an upper margin of the outer radial surface 44 and an upper margin of the inner radial surface 43, and a lower lateral surface 46 extending between a lower margin of the outer radial surface 44 and a lower margin of the inner radial surface 43. The core 41 comprises at least one pharmaceutically active ingredient dispersed in at least one excipient. In addition to the embodiment of FIG. 3, the embodiment of FIG. 4 has an upper layer 47 and a lower layer 48 as described above with reference to FIG. 2. The present invention is not limited to a tablet having an upper layer and a lower layer, but to any tablet having a plurality of layers. The layered core 41 has a coating 49 of high molecular weight water soluble polymer substantially covering the outer radial surface 44, the upper lateral surface 45 and the lower lateral surface 46, including the upper and lower layers 47, 48. The inner radial surface 43 is not covered. The coating 49 does not contain a pharmaceutically active ingredient. The high molecular weight polymer preferably has a number-average molecular weight of at least 10,000. The coating 49 provides the time delay effect discussed above.

Figure 11:
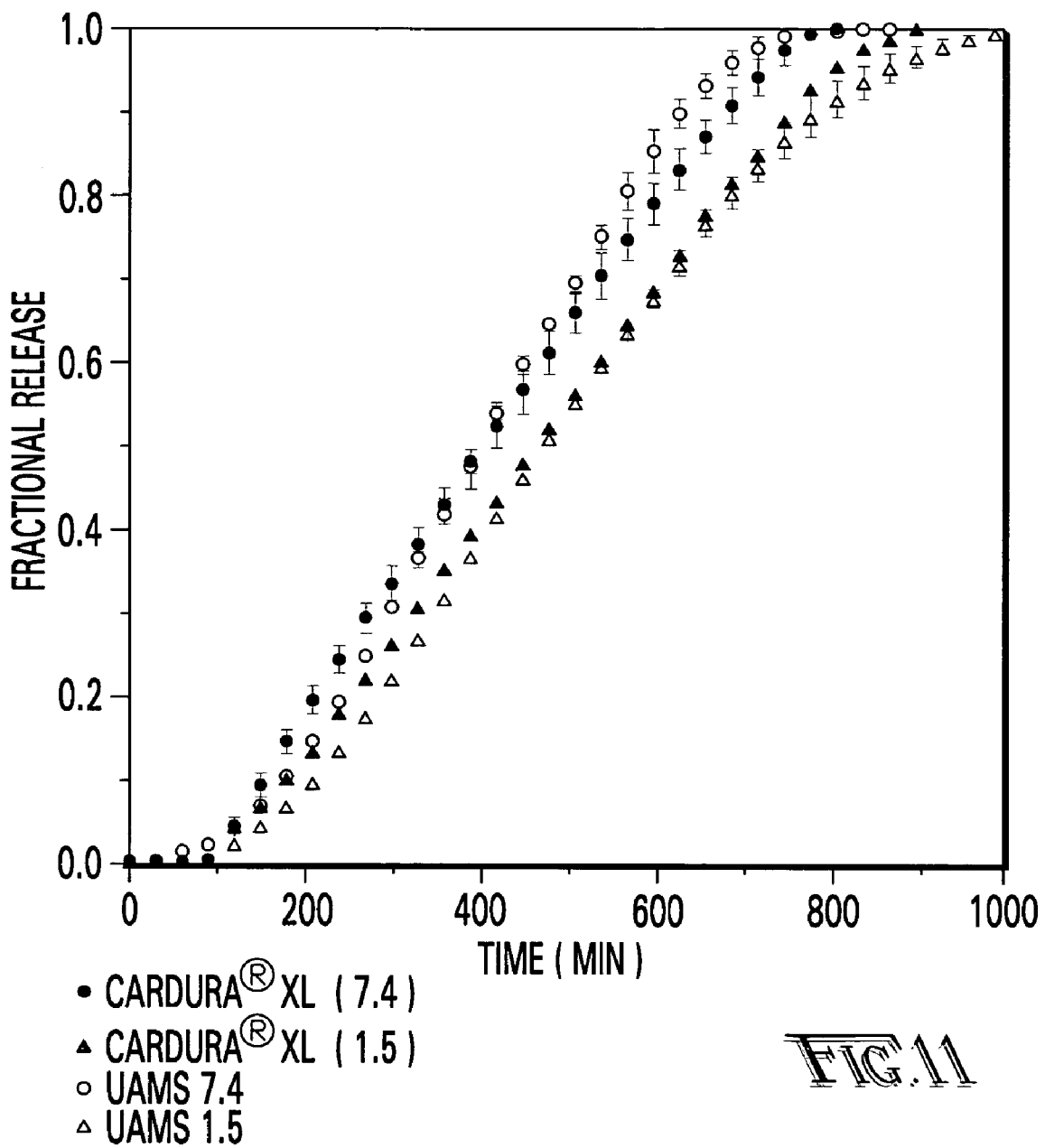
FIG. 11 is a graph of the release rate of doxazosin mesylate from the embodiment of the tablet of FIG. 4 superimposed on a graph of the release rate of a commercially-available brand of doxazosin mesylate, Cardura® XL (Pfizer Inc., New York, N.Y. USA).
Figure 12:
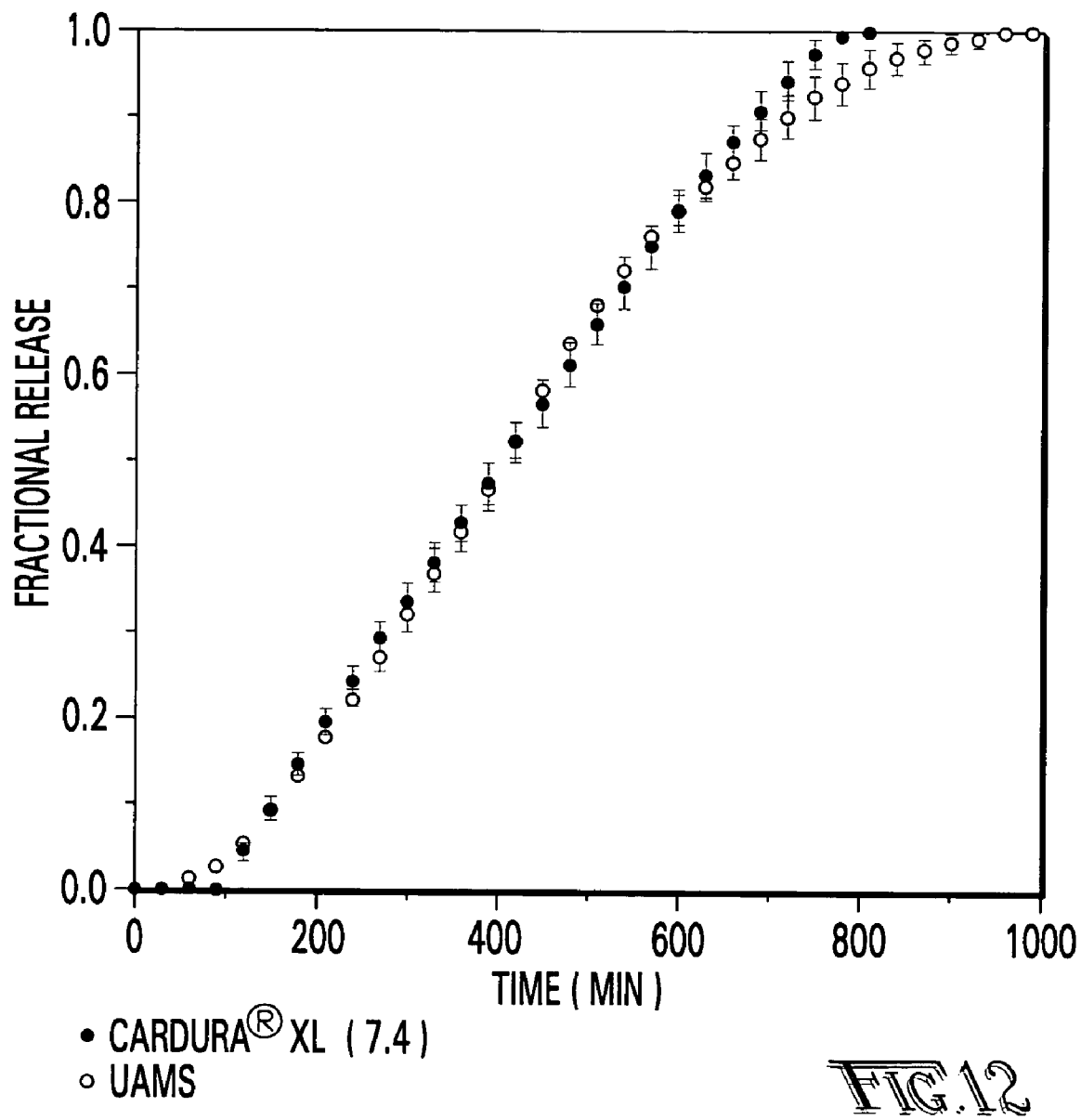
FIG. 12 is a graph of the release rate of doxazosin mesylate from the embodiment of the tablet of FIG. 4 superimposed on a graph of the release rate of a commercially-available brand of doxazosin mesylate, Cardura® XL (Pfizer Inc., New York, N.Y. USA).

FIG. 11 is a graph of the release rate of doxazosin mesylate from the embodiment of the tablet of FIG. 4 superimposed on a graph of the release rate of a commercially-available brand of doxazosin mesylate, Cardura® XL (Pfizer Inc., New York, N.Y. USA). FIG. 12 is a graph of the release rate of doxazosin mesylate from the embodiment of the tablet of FIG. 4 superimposed on a graph of the release rate of a commercially-available brand of doxazosin mesylate, Cardura® XL (Pfizer Inc., New York, N.Y. USA).

FIG. 5 is a top side perspective view of a coated perforated tablet 50 according to another embodiment of the present invention. The embodiment of FIG. 5 is similar to the embodiment of FIG. 3 in having a core 51 with a hole 52 extending through the core 51. The core 51 has a surface defined by an inner radial surface 53 surrounding the hole 52, an outer radial surface 54, an upper lateral surface 55 extending between an upper margin of the outer radial surface 54 and an upper margin of the inner radial surface 53, and a lower lateral surface 56 extending between a lower margin of the outer radial surface 54 and a lower margin of the inner radial surface 53. The core 51 comprises at least one pharmaceutically active ingredient dispersed in at least one excipient. However, rather than a single coating of high molecular weight polymer, the embodiment of FIG. 5 has an inner coating 57 of a high molecular weight water soluble polymer and an outer coating 58 of a low molecular weight water soluble polymer. The inner coating 57 does not have a drug dispersed therein. The outer coating 58 has a drug dispersed therein. The high molecular weight polymer preferably has a number-average molecular weight of at least 10,000 and the low molecular weigh polymer preferably has a number-average molecular weight of less than 10,000. The outer coating 58 begins to dissolved and to release the pharmaceutically active ingredient upon exposure to the dissolution medium. The rate of this pulsatile release may be adjusted by the appropriate selection of the specific low molecular weight polymer, the number-average molecular and the thickness of the outer coating 58. The inner coating 57 provides a time delay after the pulsatile release before the outer radial surface 54, upper lateral surface 55 and lower lateral surface 56 are exposed to the dissolution medium.

Figure 13:
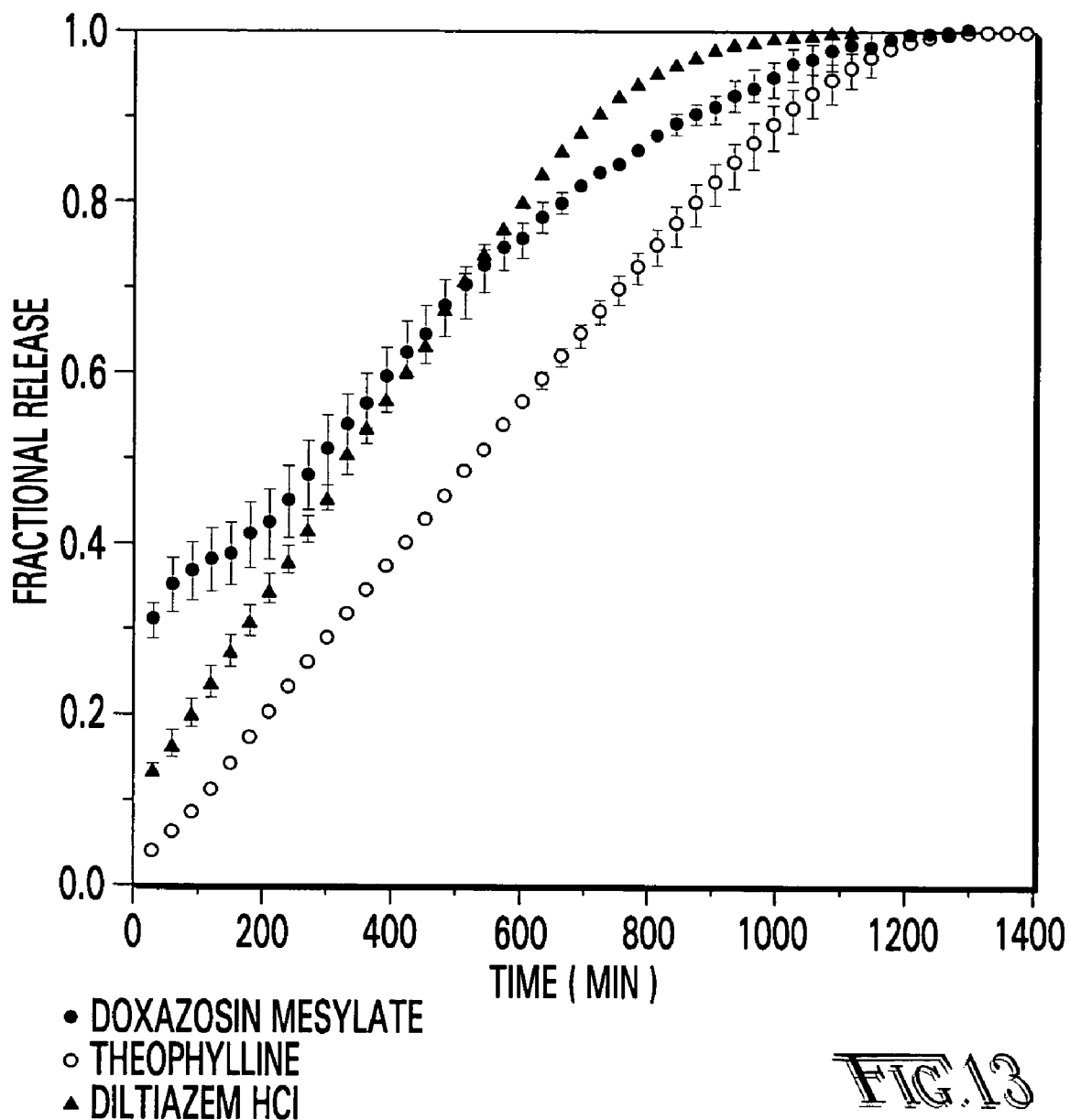
FIG. 13 is a graph of the release rates of doxazosin mesylate, theophyline and diltiazem HCl from the embodiment of the tablet of FIG. 5.

FIG. 13 is a graph of the release rate of doxazosin mesylate, theophyline and diltiazem HCl from the embodiment of the tablet of FIG. 5.

FIG. 6 is a top side perspective view of a coated layered perforated tablet 60 according to another embodiment of the present invention. The embodiment of FIG. 6 is a combination of the embodiments of FIGS. 4 and 5. The coated layered perforated tablet 60 of FIG. 6 has core 61 with a hole 62 extending through the core 61. The core 61 has a surface defined by an inner radial surface 63 surrounding the hole 62, an outer radial surface 64, an upper lateral surface 65 extending between an upper margin of the outer radial surface 64 and an upper margin of the inner radial surface 63, and a lower lateral surface 66 extending between a lower margin of the outer radial 64 surface and a lower margin of the inner radial surface 63. The core 61 comprises at least one pharmaceutically active ingredient dispersed in at least one excipient. In addition, the embodiment of FIG. 6 has an upper layer 67, a lower layer 91 and an inner layer 69 as described above with reference to FIG. 2. The present invention is not limited to a tablet having an upper layer 67, a lower layer 91 and an inner layer 69, but to any tablet having a plurality of layers. The layered cored 61 has an inner coating 68 of a high molecular weight water soluble polymer and an outer coating 92 of a low molecular weight water soluble polymer. The inner coating 68 does not have a drug dispersed therein. The outer coating 92 has a drug dispersed therein. The high molecular weight polymer preferably has a number-average molecular weight of at least 10,000 and the low molecular weigh polymer preferably has a number-average molecular weight of less than 10,000. The inner coating 68 covers substantially the outer radial surface 64, the upper lateral surface 65 and the lower lateral surface 66 including the upper and lower layers 67, 91. The inner radial surface 63 is not covered. The outer coating 92 covers substantially all of the inner coating 68 but does not cover the inner radial surface 63.

Figure 14:
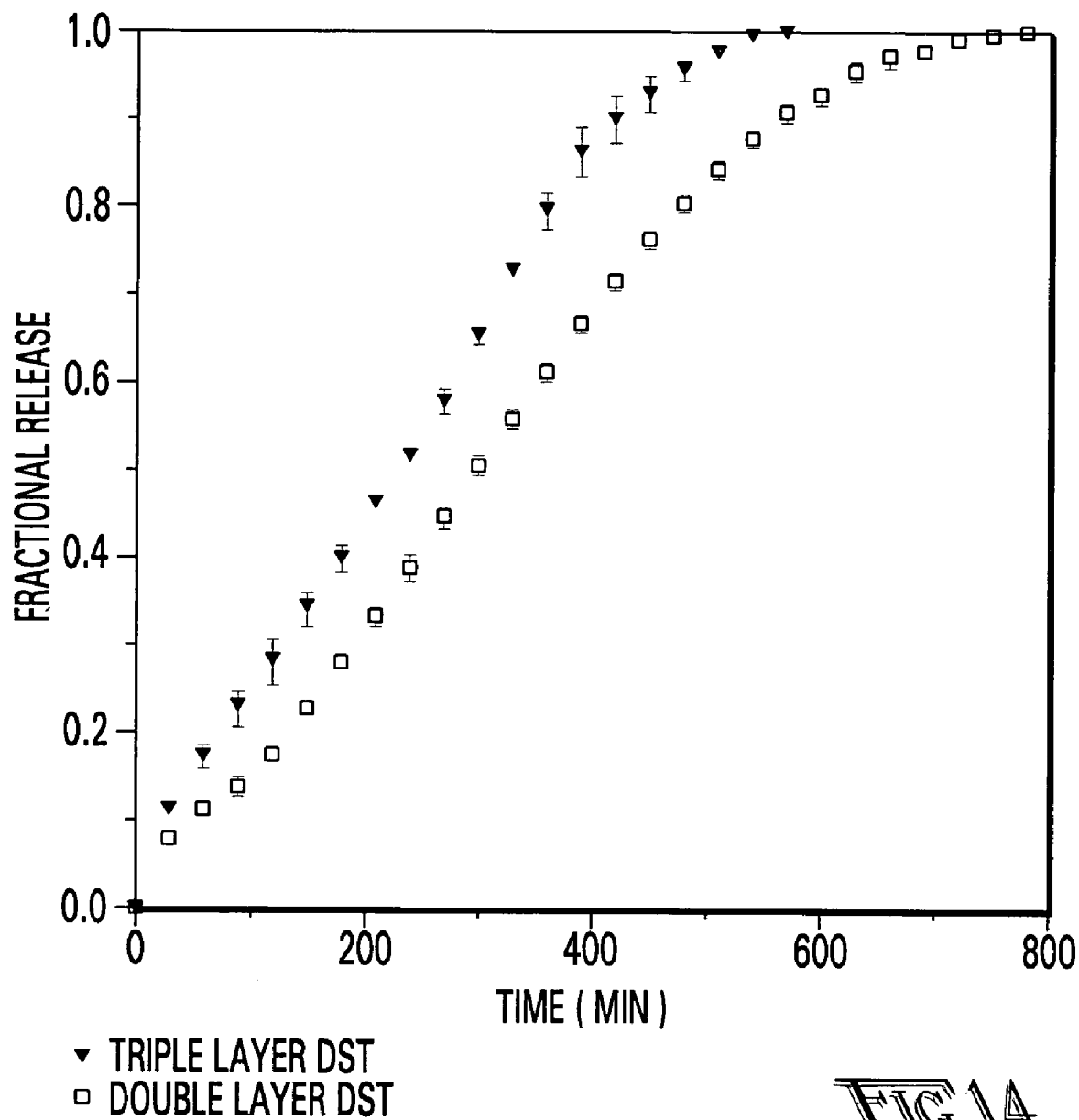
FIG. 14 is a graph of the release rate of doxazosin mesylate from the embodiment of the tablet of FIG. 6.

FIG. 14 is a graph of the release rate of doxazosin mesylate from the embodiment of the tablet of FIG. 6.

FIG. 7 is a top side perspective view of a coated perforated tablet 70 according to another embodiment of the present invention. The embodiment of FIG. 7 is similar to the embodiment of FIG. 3, but differs in that the upper lateral surface 71 slopes inwardly from the outer radial surface 72 toward the inner radial surface 73 and the lower lateral surface 74 slopes inwardly from the outer radial surface 72 toward the inner radial surface 73. In such a tablet 70, the release kinetics are altered since the surface area of the tablet 70 increases with time. The core 75 comprises at least one pharmaceutically active ingredient dispersed in at least one excipient. The coating 76 is high molecular weight water soluble polymer substantially covering the outer radial surface 72, the upper lateral surface 71 and the lower lateral surface 74. The inner radial surface 77 is not covered. The coating 76 does not contain a pharmaceutically active ingredient. The high molecular weight polymer preferably has a number-average molecular weight of at least 10,000.

FIG. 8 is a top side perspective view of a coated perforated tablet 80 with sloped upper and lower surfaces 81, 82 as described above with reference to FIG. 7. This embodiment of the present invention has an inner coating 83 of a high molecular weight water soluble polymer without a drug dispersed in the inner coating 83 and an outer coating 84 of a low molecular weight water soluble polymer with a drug dispersed in the outer coating 84.

The present invention has been described with reference to certain preferred and alternative embodiments that are intended to be exemplary only and not limiting to the full scope of the present invention as set forth in the appended claims. For example, various combinations of the embodiments described can be employed to design a dosage form for whatever release kinetics are desired.

What is claimed is:

1. A tablet for the extended release of a pharmaceutically active ingredient, comprising:
   a perforated core having a hole extending through said core, said core having a surface defined by an inner radial surface surrounding said hole, an outer radial surface, an upper lateral surface and a lower lateral surface, said core comprising at least one pharmaceutically active ingredient dispersed in at least one excipient, wherein said core comprises a plurality of layers;
   a first coating of high molecular weight water soluble polymer substantially covering said outer radial surface, said upper lateral surface and said lower lateral surface, wherein said high molecular weight water soluble polymer has a number-average molecular weight of at least 10,000; and
   a second coating of low molecular weight water soluble polymer substantially covering said first coating, said second coating having at least one pharmaceutically active ingredient dispersed therein, wherein said low molecular weight water soluble polymer has a number-average molecular weight of less than 10,000 wherein the inner radial surface is not covered by said coatings.

2. A tablet for the extended release of a pharmaceutically active ingredient, comprising:

a perforated core having a hole extending through said core, said core having a surface defined by an inner radial surface surrounding said hole, an outer radial surface, an upper lateral surface and a lower lateral surface, wherein at least one of said upper lateral surface and said lower lateral surface slope inwardly from said outer radial surface to said inner radial surface, said core comprising at least one pharmaceutically active ingredient dispersed in at least one excipient wherein said core comprises a plurality of layers;

a first coating of high molecular weight water soluble polymer substantially covering said outer radial surface, said upper lateral surface and said lower lateral surface, wherein said high molecular weight water soluble polymer has a number-average molecular weight of at least 10,000; and a second coating of low molecular weight water soluble polymer substantially covering said first coating, said second coating having at least one pharmaceutically active ingredient dispersed therein, wherein said low molecular weight water soluble polymer has a number-average molecular weight of less than 10,000 wherein the inner radial surface is not covered by said coatings.

\* \* \* \* \*